(12) United States Patent
Kroll

(10) Patent No.: US 8,700,156 B2
(45) Date of Patent: *Apr. 15, 2014

(54) HIGH ACCURACY PAINLESS METHOD FOR MEASURING DEFIBRILLATION LEAD IMPEDANCE

(71) Applicant: Mark W. Kroll, Crystal bay, MN (US)

(72) Inventor: Mark W. Kroll, Crystal bay, MN (US)

(73) Assignee: Lamda Nu, LLC, Orono, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/735,599

(22) Filed: Jan. 7, 2013

(65) Prior Publication Data

US 2013/0123871 A1    May 16, 2013

Related U.S. Application Data

(63) Continuation of application No. 12/252,310, filed on Oct. 15, 2008, now Pat. No. 8,352,033.

(60) Provisional application No. 60/999,041, filed on Oct. 15, 2007.

(51) Int. Cl.
    *A61N 1/00*       (2006.01)
    *A61B 5/00*       (2006.01)
    *A61B 5/05*       (2006.01)

(52) U.S. Cl.
    USPC ................ 607/28; 607/8; 607/27; 600/324; 600/547

(58) Field of Classification Search
    USPC ............ 600/324, 547; 607/8, 27–28
    See application file for complete search history.

(56) References Cited

U.S. PATENT DOCUMENTS

| | | |
|---|---|---|
| 3,599,055 A | 8/1971 | Bloom |
| 4,766,549 A | 8/1988 | Schweitzer, III et al. |
| 5,003,975 A | 4/1991 | Hafelfinger et al. |
| 5,231,987 A | 8/1993 | Robson |
| 5,243,980 A | 9/1993 | Mehra |
| 5,405,363 A | 4/1995 | Kroll et al. |
| 5,741,311 A | 4/1998 | McVenes et al. |
| 5,755,742 A | 5/1998 | Schuelke et al. |
| 5,897,577 A | 4/1999 | Cinbis et al. |
| 5,944,746 A | 8/1999 | Kroll |
| 6,104,954 A | 8/2000 | Blunsden |
| 6,928,325 B2 | 8/2005 | Zhu et al. |
| 7,047,083 B2 | 5/2006 | Gunderson et al. |
| 7,081,130 B2 | 7/2006 | Jang |
| 7,120,563 B2 | 10/2006 | Bechhoefer et al. |
| 7,289,851 B2 | 10/2007 | Gunderson et al. |

(Continued)

OTHER PUBLICATIONS

"Agilent Impedance Measurement Handbook A Guide to Measurement Technology and Techniques 4th Edition," Agilent Technologies, Inc., Jun. 17, 2009, 140 pages.

(Continued)

*Primary Examiner* — Nicole F Lavert
(74) *Attorney, Agent, or Firm* — Patterson Thuente Pedersen, P.A.

(57) ABSTRACT

Methods and apparatus for accurately and painlessly measuring the impedance between defibrillation electrodes implanted in a patient utilize a high current test pulse delivered with a sufficiently high current to produce an accurate measurement of the defibrillation electrode impedance while limiting the duration of the test pulse such that the pain sensing cells in the patient do not perceive the test pulse. In one embodiment, the test pulse is generated from the high voltage transformer without storing energy in the high voltage capacitors and is delivered to the defibrillation electrodes in the patient utilizing the high voltage switching circuitry.

19 Claims, 9 Drawing Sheets

(56) References Cited

U.S. PATENT DOCUMENTS

| | | |
|---|---|---|
| 7,369,893 B2 | 5/2008 | Gunderson |
| 7,747,320 B1 | 6/2010 | Kroll et al. |
| 7,764,998 B1 | 7/2010 | Raddatz |
| 8,200,330 B2 | 6/2012 | Kroll et al. |
| 8,352,033 B2 | 1/2013 | Kroll |
| 8,467,872 B2 | 6/2013 | Hareland |
| 2004/0010303 A1 | 1/2004 | Bolea et al. |
| 2004/0068301 A1 | 4/2004 | Waltman et al. |
| 2005/0187586 A1 | 8/2005 | David et al. |
| 2005/0256547 A1 | 11/2005 | Stahmann et al. |
| 2006/0135886 A1 | 6/2006 | Lippert et al. |
| 2006/0265038 A1 | 11/2006 | Hagen et al. |
| 2008/0208271 A1 | 8/2008 | Sih et al. |
| 2008/0309351 A1 | 12/2008 | Stewart et al. |
| 2009/0099615 A1 | 4/2009 | Kroll |
| 2010/0228307 A1 | 9/2010 | Kroll et al. |
| 2011/0054554 A1 | 3/2011 | Swerdlow |
| 2011/0054558 A1 | 3/2011 | Gunderson et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins,"NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Charactertization of Different Subsets of Atrial Fibrillation in General Practice in France: The ALFA Study," The College of French Cariologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by in Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

PO Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

PO, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc. Electrophysiol., 2001, pp. 592-599.

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by high-Grequency Biphasic Electrical Currents," IEEE T-BME, 2005, p. 1323.

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Application and File history for U.S. Appl. No. 12/868,056, filed Aug. 25, 2010. Inventor Swerdlow.

Application and File history for U.S. Appl. No. 12/252,310, filed Oct. 15, 2008. Inventor: Kroll.

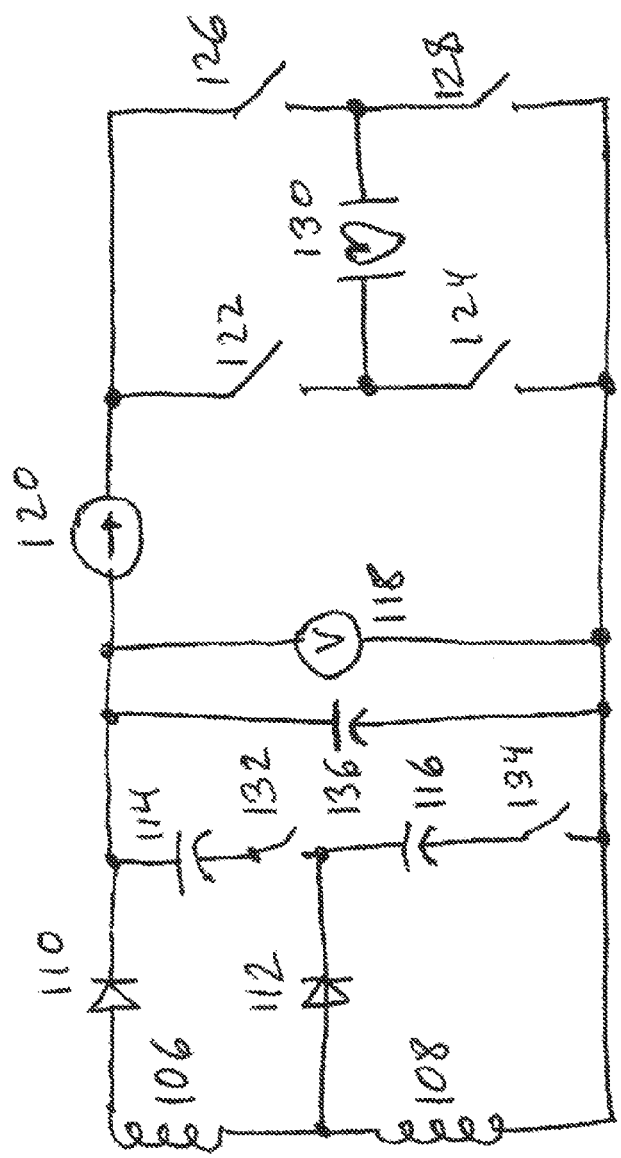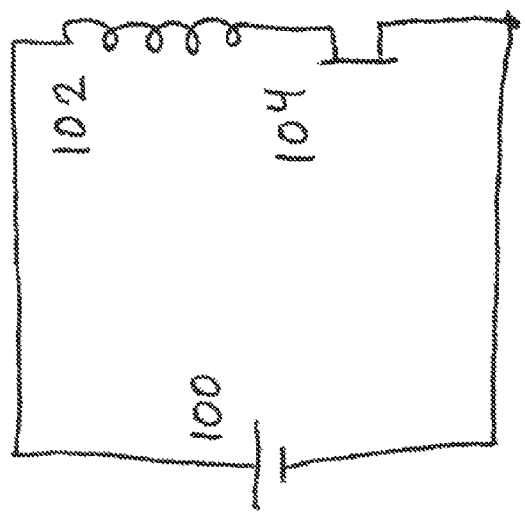
Fig. 9

HIGH ACCURACY PAINLESS METHOD FOR MEASURING DEFIBRILLATION LEAD IMPEDANCE

CROSS-REFERENCE TO RELATED CASES

This application is a continuation of U.S. patent application Ser. No. 12/252,310, filed Oct. 15, 2008, now U.S. Pat. No. 8,352,033, issued Jan. 8, 2013, which claims priority to U.S. Provisional Patent Application No. 60/999,041, filed on Oct. 15, 2007, the disclosures of which are hereby incorporated by reference.

FIELD OF THE INVENTION

The present invention relates generally to improvements for implantable medical devices such as devices for delivering defibrillation current to a body. More particularly, the invention relates to an implantable medical device that determines the impedance between defibrillation electrodes without causing pain to the body.

BACKGROUND OF THE INVENTION

Implantable cardioverter defibrillators (ICDs) are used to provide various types of therapy to a cardiac patient, including, for example defibrillation. These devices consist of a hermetic housing implanted into a patient and connected to at least one defibrillation electrode. The housing of the ICD contains electronic circuitry for monitoring the condition of the patient's heart, usually through sensing electrodes, and also contains the battery, high voltage circuitry, and control circuitry to generate, control, and deliver the defibrillation shocks. Typically, one or more defibrillation leads are connected to circuitry within the ICD and extend from the housing to one or more defibrillator electrodes proximate the heart. The housing of the ICD may include one or more defibrillation electrodes configured on the exterior of the housing. One example of an ICD is disclosed in U.S. Pat. No. 5,405,363 to Kroll et al., the disclosure of which is hereby incorporated by reference.

One important parameter for the effective operation of an ICD device is the defibrillation electrode impedance. This impedance is indicative of the positioning and integrity of the defibrillation leads and/or electrodes. Electrode impedance is also related to the defibrillation threshold for a given patient used in setting the energy levels for defibrillation shocks for that patient. Successful cardiac defibrillation depends on the amount of energy applied to the cardiac tissue by the electrical defibrillation shock, and the energy of the defibrillation shock is dependent on the electrode impedance of the defibrillation electrodes through which the defibrillation shock is delivered.

Determining the impedance between defibrillation electrodes is used in different ways when implanting and operating an ICD. One use is to allow a physician to verify that the defibrillation leads and/or electrodes have not shifted after an initial placement. Another use is to permit the physician to adjust waveform durations in the event of a significant impedance change. Still another use is to confirm the viability and settings appropriate for a defibrillation shock prior to delivering the defibrillation shock. Thus, it can be seen that accurate knowledge of the electrode impedance is important both during implantation and operation of an ICD device.

Presently, ICD devices periodically measure the impedance across the defibrillation leads by using a low voltage monophasic or alternating square wave pulse on the order of 10 volts. Most ICD devices use a low voltage monophasic pulse that is generated from the battery, rather than the high voltage capacitors that are used to generate and deliver a defibrillation shock. This is done both to keep the test shock at a level that is below the pain or perception level that may be felt by a patient, and to minimize the drain on the battery in order to periodically supply these test shocks.

With a normal defibrillation shock, the current passed through the defibrillation electrodes is on the order of ten amperes and several hundred volts and many charge carriers in the cardiac tissue are recruited to carry this current. When the cardiac tissue is subjected to a lower current pulse, fewer charge carriers are recruited to carry the lower current. As a result, the impedance of the cardiac tissue in response to a lower current pulse increases significantly. For example, a forty ohm ($\Omega$) defibrillation pathway might have an apparent impedance of over 120$\Omega$ with a lower voltage and correspondingly lower current pulse. This differential behavior of cardiac tissue in response to different amounts of current is discussed by Brewer J E, Tvedt M A, Adams T P, and Kroll M W in Low Voltage Shocks Have a Significantly Higher Tilt of the Internal Electric Field Than Do High Voltage Shocks, PACING AND CLINICAL ELECTROPHYSIOLOGY Vol. 18, p. 214 (January 1995), the disclosure of which is hereby incorporated by reference.

Because this differential behavior of cardiac tissue is known, current ICD devices using a low voltage pulse to measure the impedance of defibrillation electrode will generate a measured value that can be as much as three times greater than the actual defibrillation impedance encountered for a high voltage, high current defibrillation shock. Consequently, current ICD devices typically divide the impedance measured in response to a low voltage test pulse by some kind of "fudge" factor (e.g., 2 or 3) to estimate the actual impedance. Unfortunately, the fudge factor is not consistent with all types of leads, electrodes, patients, or changing electrolyte concentrations. Thus, significant errors are often introduced that may yield inconsistent impedance measurements.

One approach to reducing the errors induced by the use of low voltage test shocks for measuring defibrillation electrode impedance is described in U.S. Pat. No. 6,104,954 to Blunsden. In one embodiment, a square wave generator is described to generate a test pulse of approximately 50 V and 100 Khz. While this approach would somewhat improve the accuracy of the impedance measurement, unfortunately this embodiment is completely impractical for an ICD device as the continuous power requirement to implement this kind of square wave test pulse would be 50 W, an amount which is well above any continuous power supply that can be provided by current defibrillation battery technology of an ICD device.

In another embodiment, Blunsden describes the use of a higher voltage shock in the range of defibrillation voltages that is delivered from the high voltage capacitors in the ICD as a shorter test shock for purposes of measuring defibrillation electrode impedance. The approach has the advantage testing not only the defibrillation electrodes, but also the operation of the high voltage switches used to generate biphasic pulses that are typically used for defibrillation shocks. While this approach has the added advantage of exercising the high voltage switches and can address some of the errors induced by the use of low voltage test shocks, the approach introduces the possibility of unwanted shocks in the event of a failure of the high voltage switches or heightened sensitivity of the patient to larger voltage shocks. The approach also requires an increase in the drain on the battery required in order to periodically charge the high voltage capacitors to deliver these defibrillation range shocks for measuring the defibrillation electrode impedance where the vast majority of the energy required to charge the high voltage capacitors is ultimately wasted.

Defibrillation strength shocks (approximately ten amperes and several hundred volts) are extremely painful and cannot be given to conscious patients. Accurately measuring the defibrillation electrode impedance is important to effective operation of an ICD device. There is an unfulfilled need to accurately measure the actual impedance between defibrillation electrodes while minimizing or eliminating the sensation of pain felt by the patient and not adversely affecting the overall performance of the ICD device.

SUMMARY OF THE INVENTION

The present invention is directed to apparatus and methods for accurately measuring the impedance between defibrillation electrodes of an ICD device. In one embodiment, high current test pulse of a very short duration are delivered to determine the impedance between defibrillation electrodes. These short duration and high current test pulses are delivered at a voltage of at least about 75V but below the normal range of defibrillation shocks of 250-800V. Unlike current low voltage test pulse techniques, the high current test pulses produce more accurate impedance measurements. Because the pulses are shorter than the time periods required to sense pain by the human pain sensors, the high current test pulses are not perceived and therefore not painful to the patient.

In one embodiment, a biphasic test pulse is used to measure the impedance of the defibrillation electrodes. In accordance with this aspect of the invention, it is recognized that a short biphasic test pulse, with appropriately balanced phases, will have even less perception than a short monophasic test pulse. This is because the second half of the pulse, the negative phase, tends to cancel out the nascent response forming on nociceptor (pain sensing) cells.

One aspect of this invention is the use of short high current test pulses to automatically monitor the defibrillation electrode impedance and alert the patient and/or physician in the case of a significant deviation of the impedance from expected values. Another aspect of this invention is the use of short high current test pulses to automatically monitor the defibrillation electrode impedance and adjust waveform and/or defibrillation vectors in the case of a significant deviation of the impedance from expected values.

A further aspect of this invention is the use of lower charge monophasic/biphasic test pulses on the order of 2 microcoulombs (μC) to give imperceptible but highly accurate impedance measurements. A still further aspect of this invention is the use of lower charge monophasic/biphasic test pulses on the order of 20 μC to give painless but highly accurate impedance measurements, although it may be possible that some patients may perceive these 20 μC pulses.

In one embodiment, a capacitor arrangement separate from the main high voltage defibrillation capacitors is used in connection with the high voltage inverter/transformer and the high voltage switching circuit to isolate the main high voltage defibrillation capacitors from the defibrillation electrodes during impedance testing. Unlike the prior art techniques, this embodiment permits a practical and efficient use of the ICD battery to power the test pulses while accomplishing more accurate impedance measurements. It also serves to insulate the patent from an unintentional shock of normal defibrillation magnitude as the result of a device failure by ensuring that the main defibrillation capacitors are only charged when treatment is necessary and are not required to be charged during impedance testing.

BRIEF DESCRIPTION OF THE DRAWINGS

The invention may be more completely understood in consideration of the following detailed description of various embodiments of the invention in connection with the accompanying drawings, in which:

FIG. 9 depicts an ICD output circuit with an additional capacitor and switches to accurately determine impedance according to one embodiment of the invention.

Figure 1:
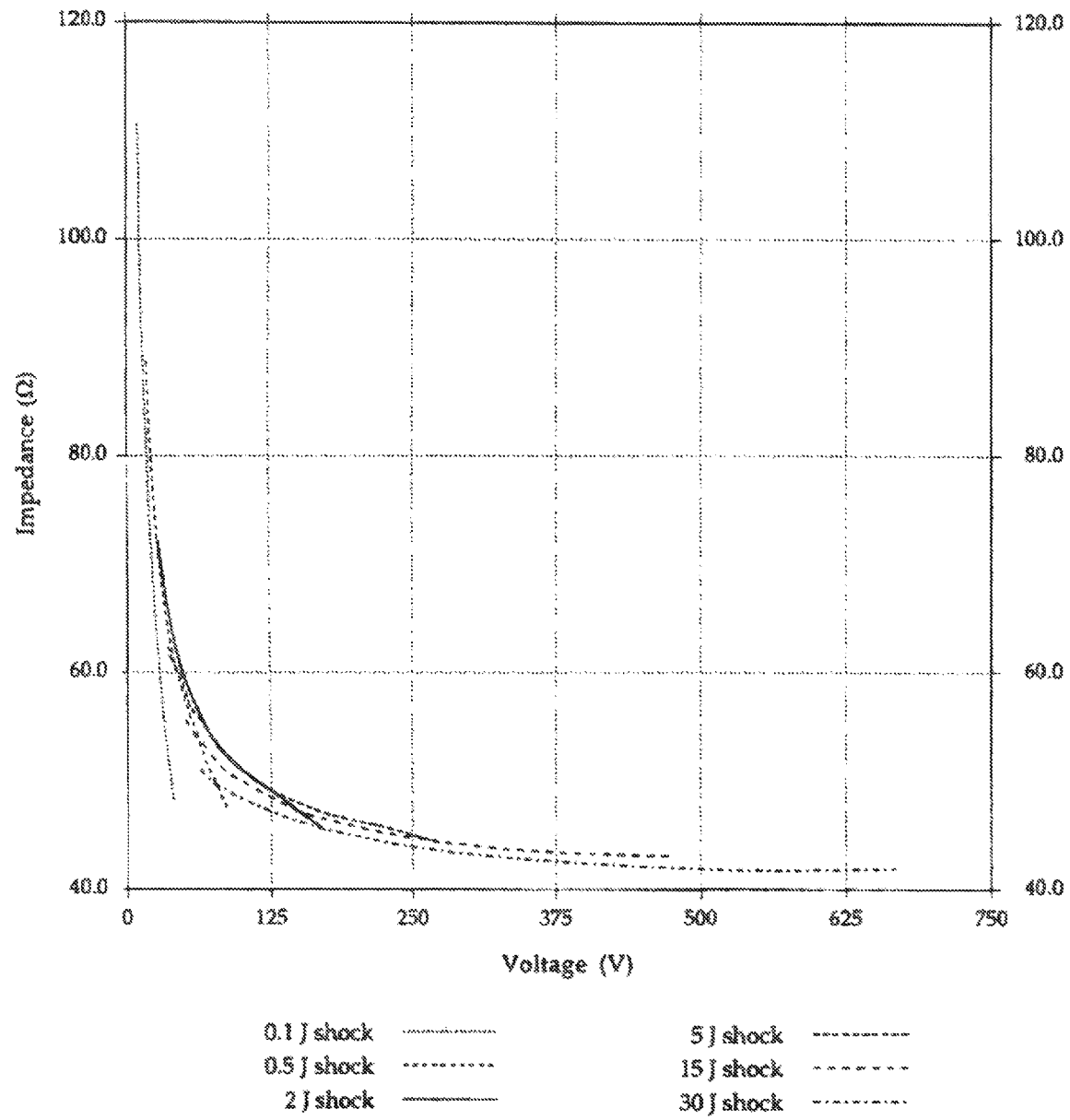
FIG. 1 depicts the relationship between voltage and measured impedance for various shock energies.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

As seen in FIG. 1 the measured impedance is highly dependent on the impressed voltage and the current used. The following calculation yields the voltage required to obtain a 10% error in the impedance. As also shown in FIG. 1, the measured impedance for a typical defibrillation electrode system is giving by:

$$Z=41+(960/V)-(2041/(V^2))$$

where V is the impressed voltage. For larger voltages the last term is insignificant. Thus the measured impedance can be estimated by:

$$Z=41+(960/V)$$

where the actual (high voltage) impedance was 39.4Ω. Thus, to calculate the voltage for a 10% error (approximately 4 ohms), set:

$$4+39.4\Omega=43.4=41+(960/V)$$

which reduces to 2.4=(960/V), yielding a value for V of 400 volts. For the impedance of 40Ω, this equates to a required current of ten amperes which would be extremely painful to a conscious person. However, as show in FIG. 2, even test pulses of one ampere can give significant accuracies beyond that seen with conventional approaches at lower current levels.

Figure 2:
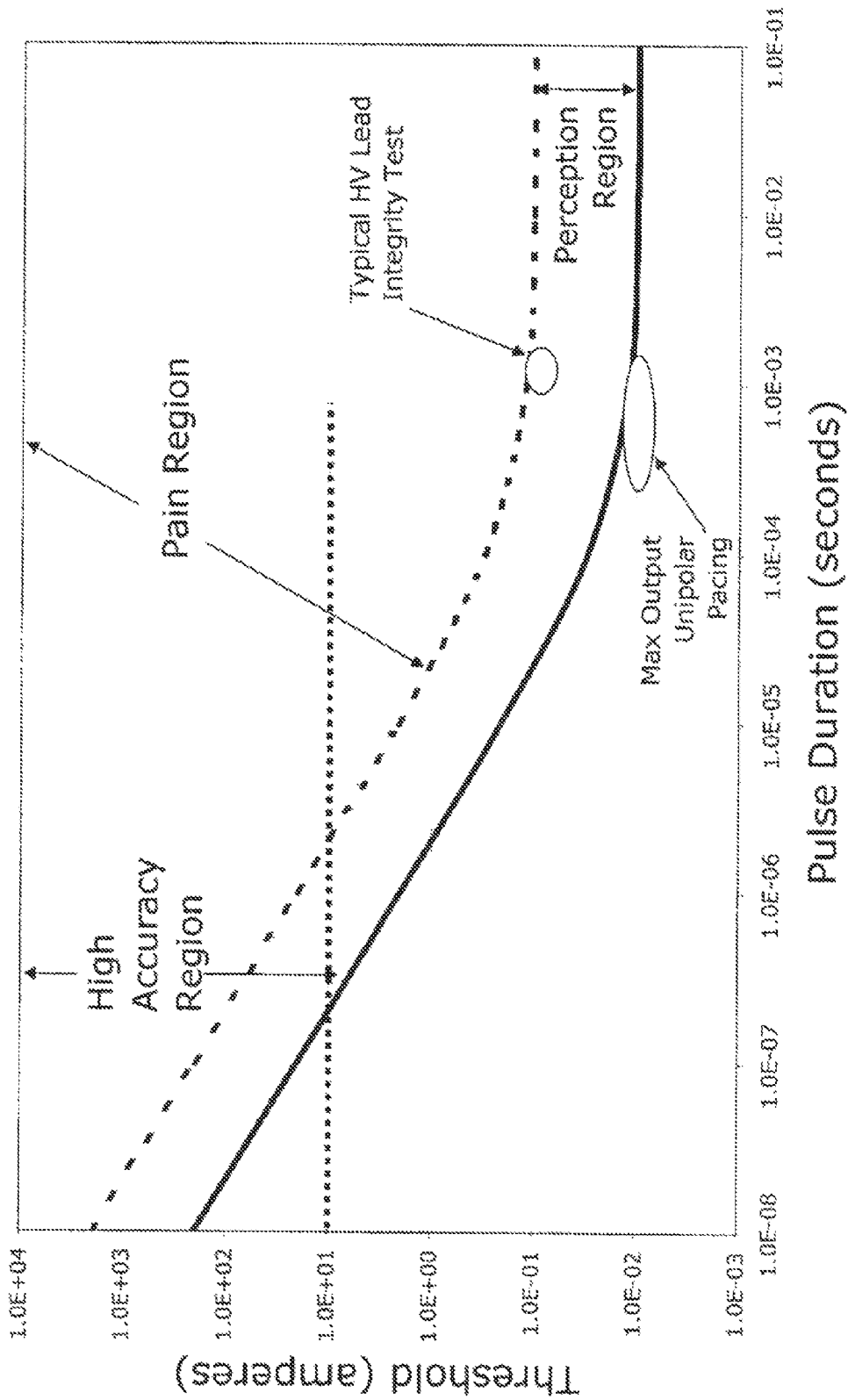
FIG. 2 depicts the relationship between the magnitude and duration of a monophasic pulse of electrical current and the threshold where that current pulse is perceived.

As depicted in FIG. 2, the threshold current for perception of an electrical pulse is a hyperbolic function of the pulse duration. For the pulses of duration exceeding the "chronaxie" of pain receptors the threshold current is fairly constant. The chronaxie value for pain receptors shown in FIG. 2 is conservatively valued at 200 microseconds. (The use of a higher value such as 400 microseconds will give more optimistic predictions for the benefit of this invention.) However, below the chronaxie pulse duration, the threshold for perception and pain go up inversely with the pulse duration. Thus the perception threshold is about 3 amperes for a 1 microsecond pulse. The typical pain threshold shown in FIG. 2 is at about ten times the perception threshold. The pain threshold has a similar inverse relationship with the pulse duration.

The typical maximum unipolar pacing output of 10 mA at 1 millisecond or less is also shown. Patients often perceived this level of stimulation. This area is considered by those skilled in the art to be at the perception edge of most patients. The typical high voltage (HV) lead integrity test level of 100 mA is also depicted at the edge of the pain region.

FIG. 2 also depicts a triangular region (with log-log plotting) which is above the 10 amperes required for accuracy and also below the current levels where the current is perceived. This region is defined by a pulse with a duration of 0.3 microseconds or less. This is also for pulse of total charge less than 2 μC. The result of these calculations is that this small region provides for an accurate measurement of the impedance without the patient perceiving the shock.

With a biphasic shock the net charge delivered can be set to zero coulombs by having essentially equal first and second phases. The result of this is that the perception and pain thresholds are increased by at least a multiple of five.

Figure 3:
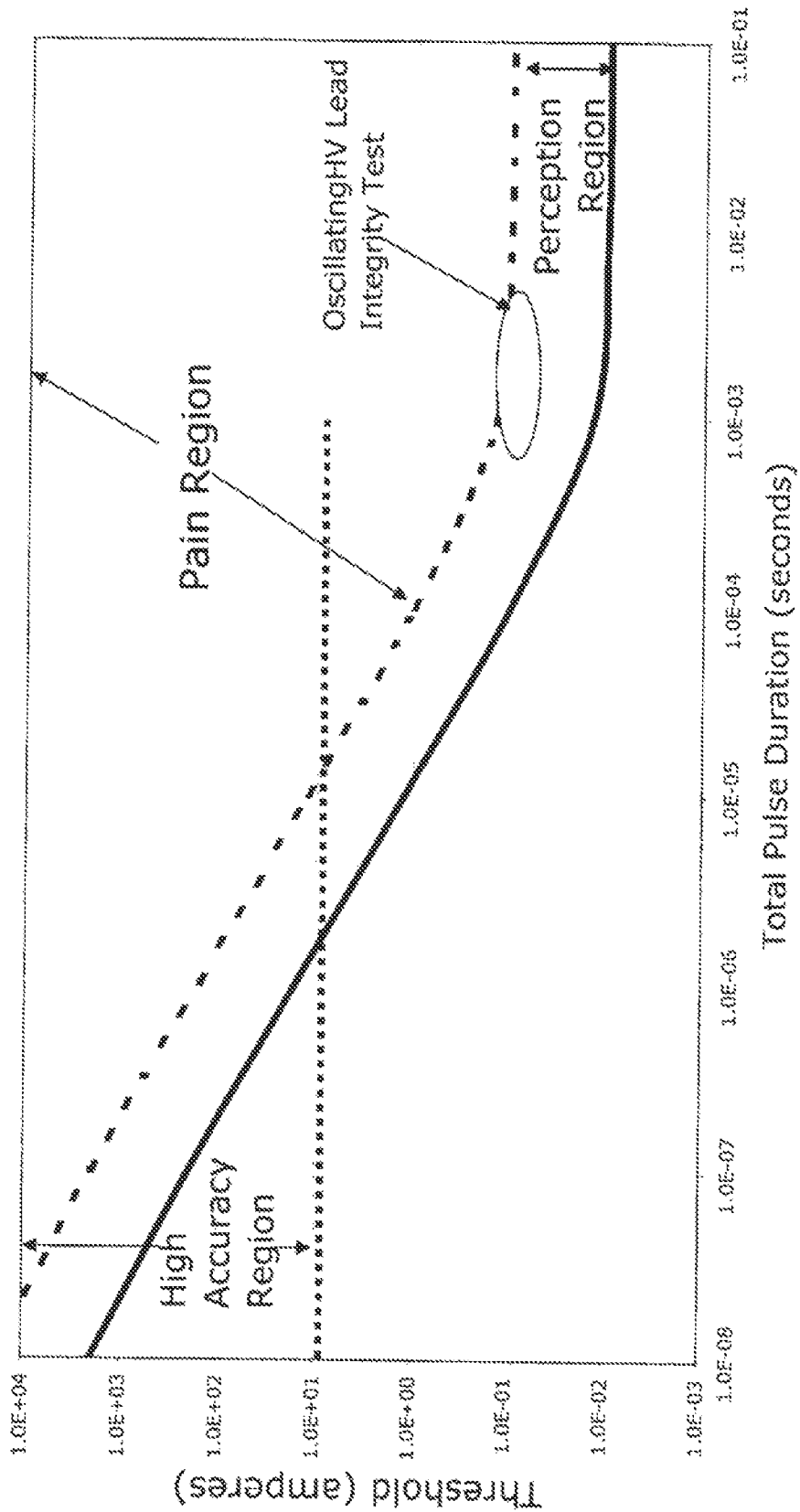
FIG. 3 depicts the relationship between the magnitude and duration of a balanced biphasic pulse of electrical current and the threshold where the current pulse is perceived.

In FIG. 3 the increased thresholds are depicted and the pulse duration plotted is the "total" duration of both phases of a biphasic shock. Since this gives a first phase duration of one-half of the total, the threshold current is multiplied by two; in addition to the multiplication by five from the second phase cancellation effects. This results in the perception and pain threshold currents being multiplied by a factor of ten for short pulses. Thus, for a biphasic pulse, the region for an imperceptible—yet high accuracy—impedance test is expanded to include pulses with durations out to about 2 micro-seconds. The allowable total (rectified) charge is increased to about 20 microcoulumbs. Thus, the biphasic impedance test waveform is the preferred embodiment of this invention.

Figure 4:
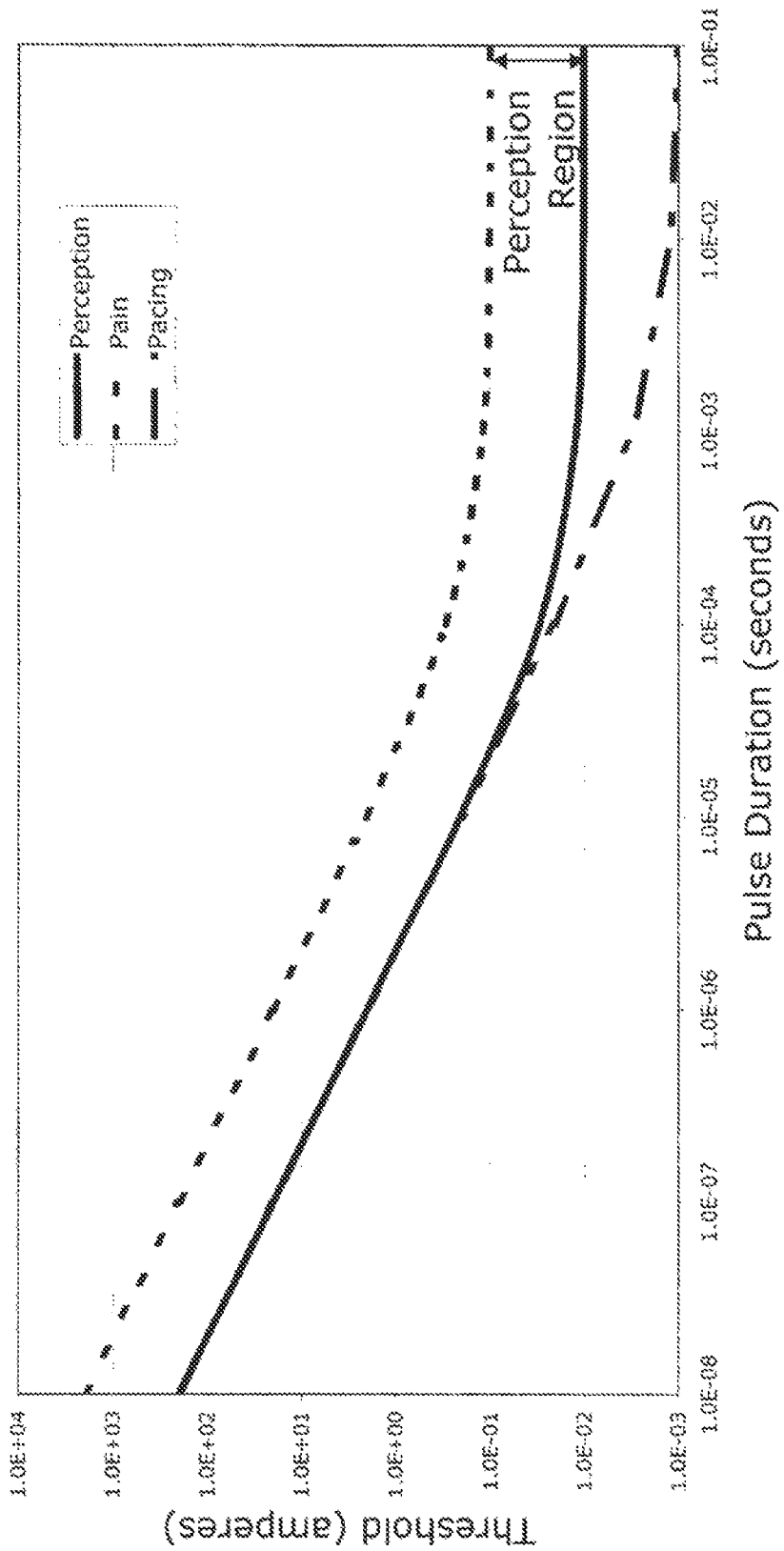
FIG. 4 depicts the relationship between the magnitude and duration of a monophasic pulse of electrical current relative to pain and perception thresholds.

Another significant advantage of this invention is the ability to accurately measure impedance without affecting the heart. As seen in FIG. 4, the monophasic cardiac stimulation threshold is above that of perception for pulses shorter than 10 microseconds. This is based on the cardiac chronaxie for large electrode stimulation of about 2 milliseconds.

Figure 5:
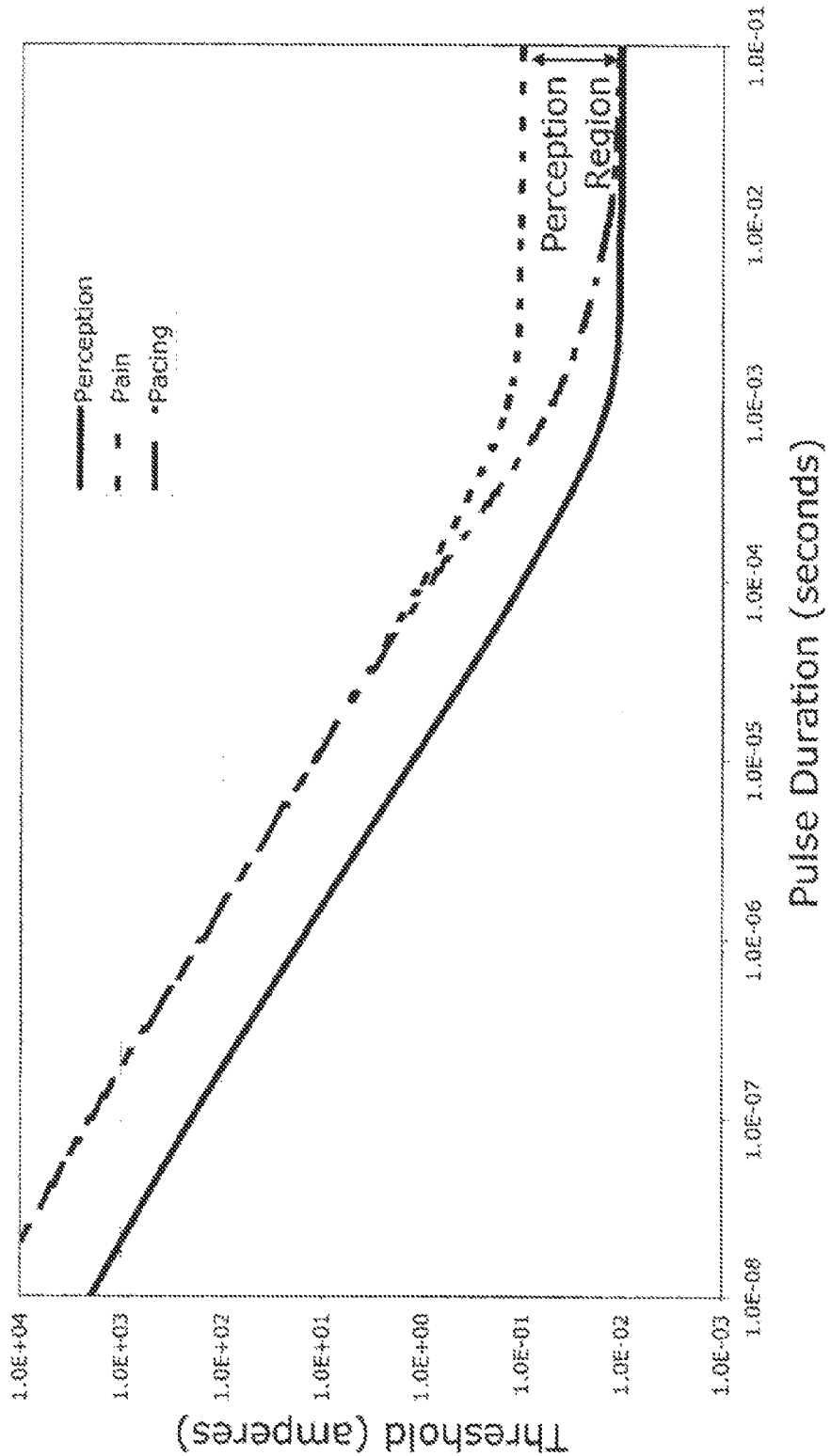
FIG. 5 depicts the relationship between the magnitude and duration of a balanced biphasic pulse of electrical current relative to pain and perception thresholds.

As seen in FIG. 5, the biphasic cardiac stimulation threshold is above that of pain for pulses shorter than 30 microseconds. Thus these test pulses can be given without fear of any cardiac effect. To add further safety, the pulses may be given synchronized with the QRS complex.

Figure 6:
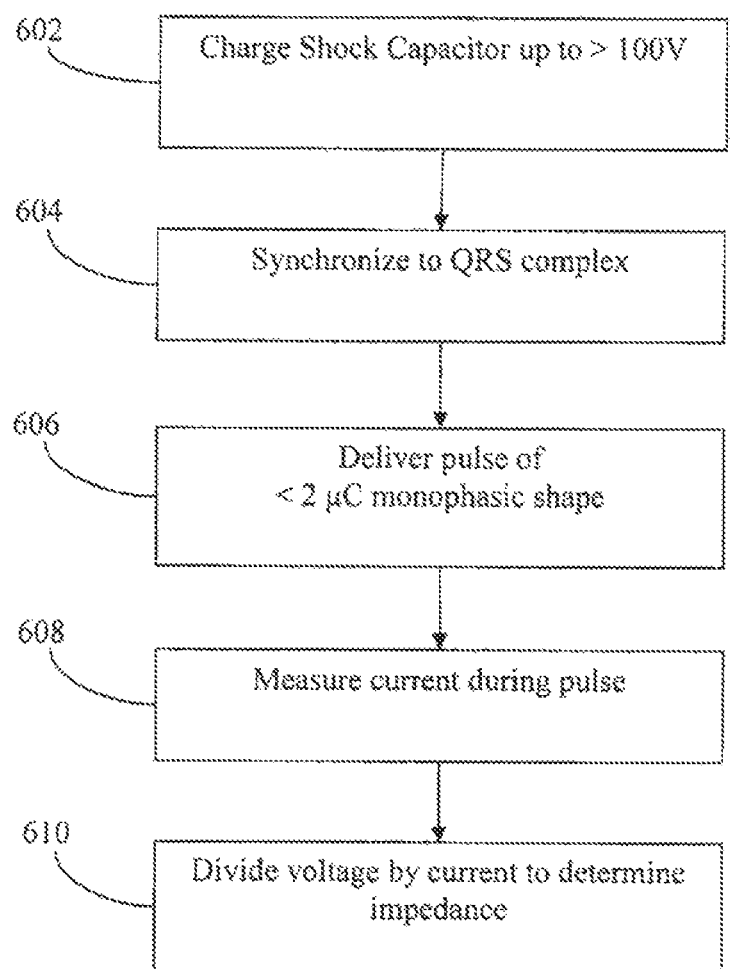
FIG. 6 illustrates generally a flow chart diagram of steps to accurately determine impedance according to one embodiment of the invention.
Figure 7:
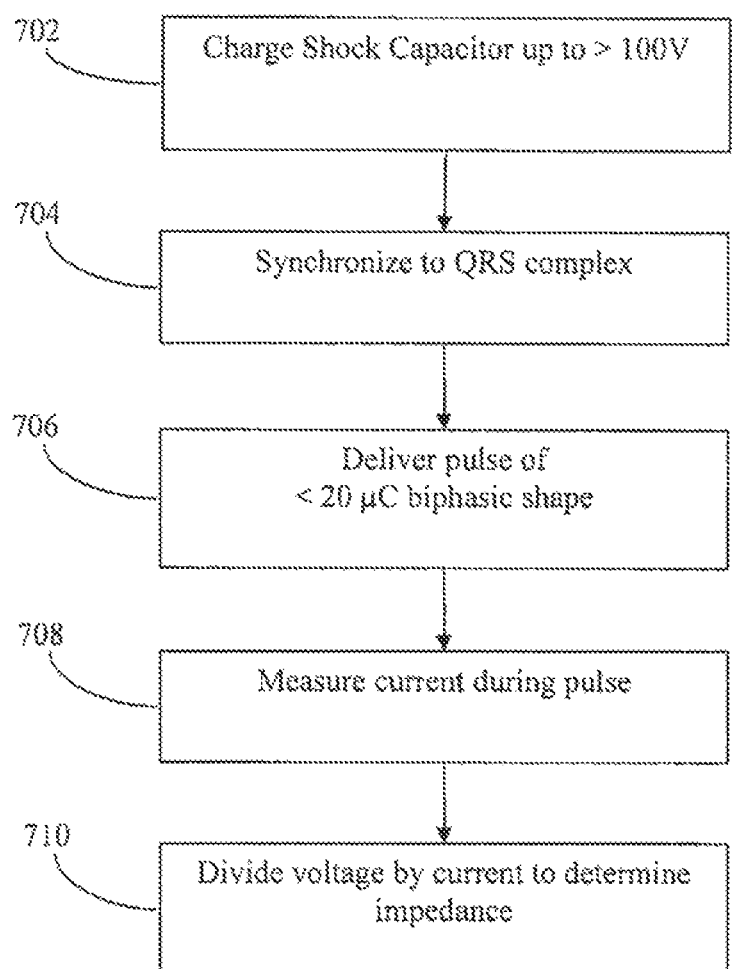
FIG. 7 illustrates generally a flow chart diagram of steps to accurately determine impedance according to one embodiment of the invention.

One method of practicing an embodiment of this invention is shown in FIGS. 6 and 7. First, a shock capacitor located in an implantable cardiovascular defibrillator is charged to a potential of below a conventional defibrillation range corresponding to therapeutic defibrillation shock energies of at least about 5 J, which equate to a typical charge voltage of at least about 250V. Preferably, this will be a charge voltage for the high current test pulse of between about 75-250V, and optimally between about 100-150V. Second, the defibrillator synchronizes delivery of a test pulse to the QRS complex of the heart. Third a synchronized monophasic shaped pulse of less than 2 microseconds, or biphasic shaped pulse of less than 20 microseconds, is delivered to the heart through the defibrillator electrodes. Fourth, the current level is measured during the pulse. Finally, the voltage is divided by the current to determine the impedance between the defibrillation electrodes.

Figure 8:
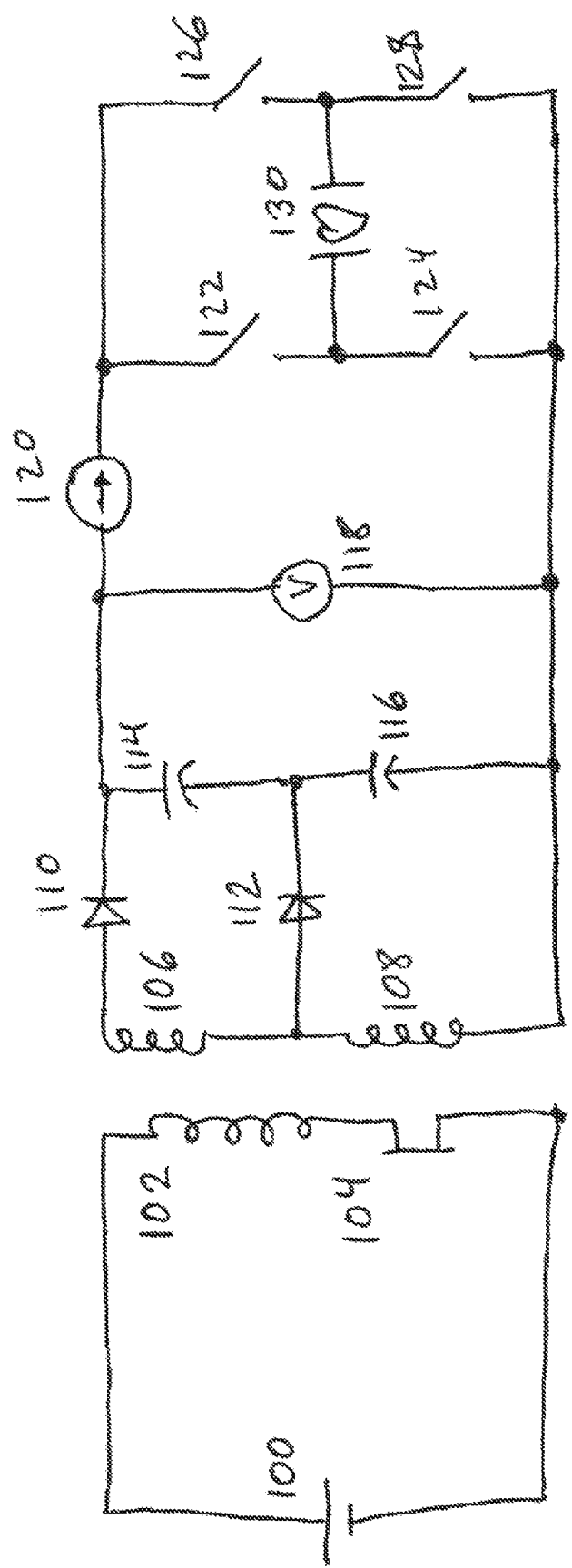
FIG. 8 depicts a conventional ICD output circuit capable of delivering monophasic or biphasic pulses to a heart.

A conventional ICD output circuit is shown in FIG. 8. Battery 100 delivers current to transformer primary 102 when switch 104 is closed. When switch 104 is opened a "flyback" current is generated by the secondaries 106 and 108 which passes through diodes 110 and 112 to charge main capacitors 114 and 116 which have typical values of 150-300 μF each. Voltage sensor 118 monitors the total capacitor voltage and stops the charging when the capacitor bank has achieved the desired final voltage for a therapeutic defibrillation shock which is in the range of 250-800 volts. The defibrillation shock is delivered to the heart 130 through electrodes by briefly (3-6 milliseconds) closing switches 122 and 128 for a first phase followed by briefly (3-6 milliseconds) closing switches 124 and 126 to deliver a reversed polarity second phase. The signal from current sensor 120 is divided into the voltage from sensor 118 to obtain the real-time impedance of the electrodes and the heart.

This conventional ICD system can provide accurate impedance measurements during a high voltage shock. However, it provides very inaccurate readings (up to 300% error) when used with conventional lower voltage (10-15 V) test pulses due to the extreme nonlinearity of the resistance in the electrode-electrolyte interface.

By way of example, FIG. 9 depicts one embodiment of the present invention. A small (approximately 1 nF to 1 μF in value) capacitor 136 is added in parallel with the main capacitors 114 and 116. In normal operation this small capacitor 136 helps hold a high current test pulse charge and thus does not hurt volumetric efficiency of the overall design significantly. During normal defibrillation operation the new switches 132 and 134 are closed allowing the small capacitor 136 to charge in parallel with the main capacitors 114 and 116.

To accurately measure the impedance without the delivery of a defibrillation shock, switches 132 and 134 are opened. This acts to insulate the main capacitors 114 and 116 from the output circuit and the patient. The primary winding switch 104 is turned on to saturate the transformer core. The transformer will typically store about 40 μl of energy in the core. When the switch 104 is opened this energy will be transferred into capacitor 136. Using an illustrative value of 8 nF for this small capacitor 136, the voltage stored will be 100 volts given by V=(2E/C). Output switches 122 and 128 are now turned on to deliver a test pulse to the heart 130. The time constant of an 8 nF capacitor and a typical 50Ω shocking lead impedance gives a time constant of 0.4 μs. This will place the test pulse duration well within the zero-to low perception range. These values are an example embodiment and should not be read a limiting the scope of this invention. Those skilled in the art will recognize that the above values may be adjusted to practice the invention as necessary depending on the electrode lead technology used and the physical characteristics of the patient.

In another embodiment, the capacitor 136 is chosen to have a value of approximately 100 nF. In this embodiment utilizing a somewhat large capacitance value, the transformer core and switch 104 must then be cycled several times in order to bring the voltage of capacitor 136 up to a desired range for the high current test pulse of 75-250V. In one embodiment, the transformer core and switch 104 are cycled a sufficient number of time to generate a charge of approximately 100 volts on capacitor 136. The output H-bridge is then cycled to provide a very short monophasic or biphasic test pulse according to the detailed methods of this invention already described above.

It will be understood that numerous known techniques for determining the impedance of a given combination of defibrillation electrodes under test using the high current test pulse of the present invention may be utilized, such as by measuring current, voltage, capacitive decay, duration, or any combination thereof. It will be understood that the given combination of defibrillation electrodes may comprise two or more defibrillation electrodes, where the electrodes may be situated on one or more defibrillation leads, patch electrode, housing electrode or stent electrode arrangements positioned within or without the heart.

Finally, while the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The invention claimed is:

1. An automated method of determining defibrillation electrode impedance of at least a pair of defibrillation electrodes implanted proximate a heart of a patient comprising:
   applying a high current test pulse having a current greater than or equal to 1 ampere for a duration less than or equal to 3 microseconds to the defibrillation electrodes; and
   automatically determining the impedance between the defibrillation electrodes.

2. The automated method of claim 1 wherein applying the high current test pulse utilizes a monophasic test pulse of a duration less than or equal to 3.0 microseconds and greater than 0.3 microseconds.

3. The automated method of claim 1 wherein applying the high current test pulse utilizes a biphasic test pulse of duration less than or equal to 2.0 microseconds.

4. The automated method of claim 1 wherein applying the high current test pulse utilizes a biphasic test pulse of duration less than 2.0 microseconds and greater than 0.2 microseconds to the leads.

5. The automated method of claim 1 further comprising:
   synchronizing the test pulse to a QRS complex of the heart to avoid cardiac stimulation.

6. The automated method of claim 1 wherein the method is performed by an implantable cardioverter defibrillator that includes a high voltage transformer electrically connected between a battery and a high voltage capacitor configured to selectively deliver a therapeutic defibrillation shock through the defibrillation electrodes, and applying the high current test pulse is performed by the implantable cardioverter defibrillator without charging the high voltage capacitor system.

7. The automated method of claim 6 wherein, applying the high current test pulse is performed by utilizing a smaller capacitor system electrically connected to a secondary winding of the high voltage transformer and a switching arrangement that selectively switches out the high voltage capacitor system when applying the high current test pulse from the smaller capacitor system.

8. A method, comprising:
   providing an implantable cardioverter defibrillator that includes a high voltage transformer electrically connected between a battery and a high voltage capacitor configured to selectively deliver a therapeutic defibrillation shock through the defibrillation electrodes;
   providing instructions for implanting the cardioverter defibrillator in a patient, the instructions comprising:
   attaching at least a pair of defibrillation electrodes proximate a heart of the patient;
   using the implantable cardioverter defibrillator to apply a high current test pulse having a current greater than or equal to 1 ampere for a duration less than or equal to 3.0 microseconds to the defibrillation electrodes; and
   determining an impedance between the defibrillation electrodes, in response to the high current test pulse such that the impedance is determined without noticeable pain by the patient.

9. The method of claim 8 wherein applying the high current test pulse utilizes a monophasic test pulse of a duration less than or equal to 3.0 microseconds and greater than 0.3 microseconds.

10. The method of claim 8 wherein applying the high current test pulse utilizes a biphasic test pulse of duration less than or equal to 2.0 microseconds.

11. The method of claim 8 wherein applying the high current test pulse utilizes a biphasic test pulse of duration less than 2.0 microseconds and greater than 0.2 microseconds to the leads.

12. The method of claim 8 wherein the instructions further comprise:
   synchronizing the test pulse to a QRS complex of the heart prior to applying the high current test pulse in order to avoid cardiac stimulation.

13. An implantable cardioverter defibrillator comprising:
   a high voltage transformer electrically connected between a battery and a high voltage capacitor configured to selectively deliver a therapeutic defibrillation shock through at least a pair of defibrillation electrodes; and
   means for delivering a high current test pulse having a current greater than or equal to 1 ampere for a duration less than or equal to 3 microseconds to the defibrillation electrodes; and
   means for automatically determining the impedance between the defibrillation electrodes in response to the high current test pulse such that the impedance is determined without noticeable pain by the patient.

14. The implantable cardioverter defibrillator of claim 13 wherein the means for automatically determining the impedance between the defibrillation electrodes in response to the high current test pulse such that the impedance is determined without perception by the patient.

15. The implantable cardioverter defibrillator of claim 13 wherein the high current test pulse utilizes a monophasic test pulse of a duration less than or equal to 3.0 microseconds and greater than 0.3 microseconds.

16. The implantable cardioverter defibrillator of claim 13 wherein the high current test pulse utilizes a biphasic test pulse of duration less than or equal to 2.0 microseconds.

17. The implantable cardioverter defibrillator of claim 13 wherein the high current test pulse utilizes a biphasic test pulse of duration less than 2.0 microseconds and greater than 0.2 microseconds to the leads.

18. The implantable cardioverter defibrillator of claim 13 further comprising:
   means for selectively delivering a therapeutic defibrillation shock through the defibrillation electrodes, and means for applying the high current test pulse by the implantable cardioverter defibrillator without charging the high voltage capacitor system.

19. The implantable cardioverter defibrillator of claim 18 further comprising:
- a smaller capacitor system electrically connected to a secondary winding of the high voltage transformer;
- a switching arrangement that selectively switches out the high voltage capacitor; and
- means for applying the high current test pulse through the pair of defibrillation electrodes utilizing the smaller capacitor system.

* * * * *